United States Patent [19]
Allen

[11] Patent Number: 6,059,787
[45] Date of Patent: May 9, 2000

[54] COMPRESSION BONE STAPLE APPARATUS AND METHOD

[76] Inventor: Drew Allen, 3970 Teale Ave., San Jose, Calif. 95117

[21] Appl. No.: 09/299,285

[22] Filed: Apr. 26, 1999

[51] Int. Cl.[7] .................................................. A61B 17/56
[52] U.S. Cl. ............................................................. 606/75
[58] Field of Search .................................. 606/75, 77, 76, 606/72, 60; 411/450, 456, 457, 458, 459, 460

[56] References Cited

U.S. PATENT DOCUMENTS

| | | | |
|---|---|---|---|
| 4,723,540 | 2/1988 | Gilmer, Jr. | 606/75 |
| 4,838,254 | 6/1989 | Gauthier | 606/75 |
| 4,994,063 | 2/1991 | Garner | 606/75 |

*Primary Examiner*—Michael Buiz
*Assistant Examiner*—(Jackie)Tan-Uyen T. Ho
*Attorney, Agent, or Firm*—Charles E. Corbin

[57] ABSTRACT

A method and apparatus for interosseous bone fixation uses a compression staple, generally U-shaped, having a pair of legs with sharp front ends and proximal ends interconnect by a bridge portion that is resilient and bowed, the staple having an initial configuration and capable of a tensioned configuration by spreading apart the legs by a certain amount causing the curvature of the bowed bridge to lessen and the legs urged towards each other with certain compressive spring force. A staple applicator supports and guides the staple and positions the tensioned staple with its pointed ends forward, adjacent an ejection port at the front of the applicator. A powered strike member is mounted for longitudinal movement and has a front end that will strike the rear of the tensioned staple with percussive force and eject it in tensioned configuration from the applicator.

20 Claims, 3 Drawing Sheets

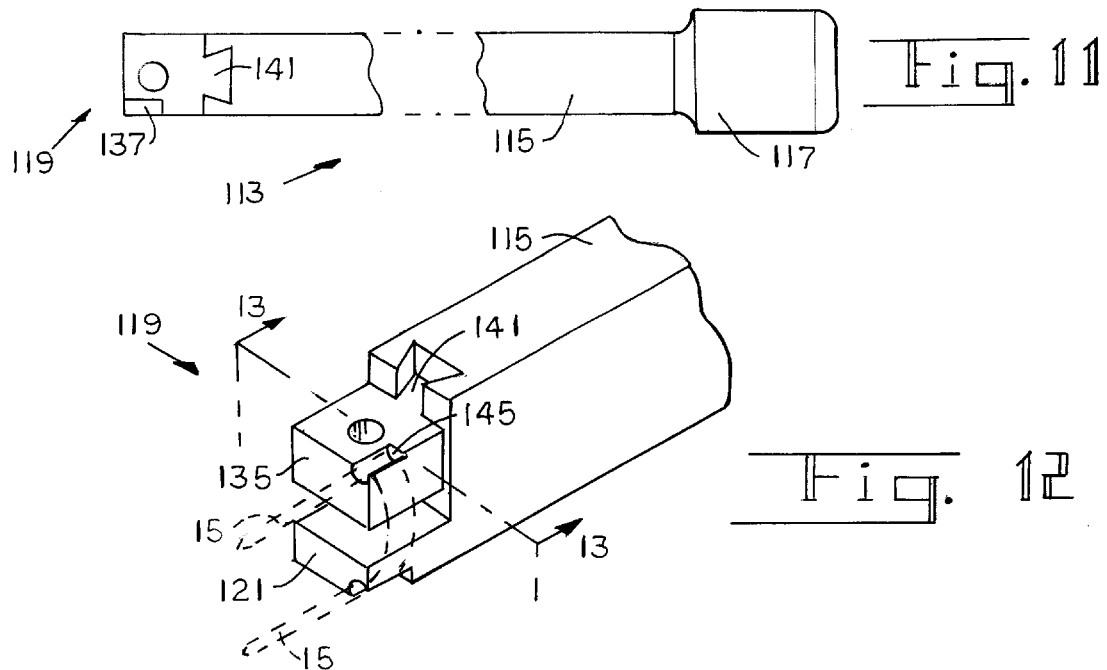

6,059,787

COMPRESSION BONE STAPLE APPARATUS AND METHOD

BACKGROUND OF THE INVENTION

1. Field of the Invention

The present invention relates to devices and techniques for securing bone segments across a fracture site, and more particularly relates to a bone stapling method and apparatus for achieving compression between segments.

2. Description of the Prior Art

In treating a bone fracture it is common practice to fasten one bone segment to the other so as to stabilize and immobilize them for the duration of the bone consolidation process. Thus there is the technique of internal fixation or direct mechanical fastening of the bone segments.

Traditionally, fixation has been accomplished by variety of apparatus and techniques, the more common involving the use of metallic fastening devices such as screws, connector plates (secured to the bone by screws), pins and clips. These methods invariably involve the drilling of screw holes in the bone and the use of related equipment such as drill hole templates. Conventional U-shaped clips have also been used, the clip legs being installed one each in holes in the opposing bone segments. The rigid structure of such clips, like the other fixation devices mentioned above, provide rigid immobilization of the fracture zone. Such devices also served to maintain the distance between segments, which was found however, among other things, to hinder compression induced by contractions of skeletal muscles in some cases, and prevent the establishment of compressive force between the bone segments which is favorable to bone consolidation or knitting. In this regard the concept of creating dynamic compressive force across an osteotomy or bone fracture site has become well recognized as a technique to promote primary bone healing, i.e. consolidation that is faster and of better quality.

Thus there has evolved a number of fastening devices such as clips and the like, designed to deliver compression. Accordingly in U.S. Pat. No. 3,939,294 there is provided a clasp or clip of spring material having a pair of spaced-apart, inwardly inclined legs connected by a Z-shaped upper portion. Sloped holes are drilled in adjoining bone segments and tools are used to manipulate and install one leg, and then the other leg is pulled toward the other hole, spreading the Z-shaped elastic portion, and then inserted in the other hole. Unfortunately this method requires the drilling of specially sloped holes, involves multiple steps and is time-consuming, and like the conventional rigid fastening techniques, requires relatively large surgical opening. Also, the manual installation of the clip using hemostats and the like is difficult, requires meticulous skill and handling.

In U.S. Pat. No. 4,838,254 the legs of a pair of metallic clips are inserted in pairs of specially angled bores in respective opposing bone segments. The exposed tops of the two installed clips then serve as fastening heads for a spring that is connected between the clips.

In U.S. Pat. No. 4,841,960 the disclosed "compression" clip is essentially a clip with opposing legs that are installed in pre-drilled holes and features a crimpable web that joins the top ends of the legs. A crimping tool is used to crimp the web in an effort to set up compression between the embedded legs.

U.S. Pat. No. 4,852,558 also requires manual installation of separate legs in pre-drilled holes, the tops of the install legs then being interconnected with a ratchet mechanism which must be operated to draw the legs together. This design appears inherently limited regarding adjustability and maintenance of constant pressure. In U.S. Pat. No. 5,660,188 the two legs of a clip must also be installed in pre-drilled holes. The clip has a bridge of two side-by-side crimpable elements, and the jaws of a crimping tool must be used on the embedded clip to deformingly spread apart these elements, causing the legs to draw to each other. The foregoing techniques involving crimpable clips all appear to be imprecise in setting up suitable compressive forces, require hole drilling and related problems, and do not lend themselves to minimizing the size of the surgical opening.

In view of the limitations of the afore-mentioned methods, stapling has been looked to as a potentially quick and effective way for fastening bone segments, and as a way to produce compression. Thus in U.S. Pat. Nos. 5,053,038 and 5,662,655 "compression" staples are applied to the bone by a powered stapler. These staples have legs shaped with beveled ends and/or have divergent legs that will be forced apart from each other during implantation, which flexes springy upper parts of the legs thereby tending to set up compression. Unfortunately there is concern for trauma to the bone due to driving of the compound-shaped legs into the bone mass, and there is little apparent precision in establishing the desired compressive forces.

SUMMARY OF THE INVENTION

In view of the foregoing it is a general object of the present invention to provide an improved method and for interosseous fastening.

A more particular object is to provide quick and simple, yet effective method for fastening bone segments with compressive force between opposing bone ends.

Another object to provide such a method that minimizes the size of the required surgical opening and associated trauma.

A further object to provide a method of bone stapling that minimizes trauma to the bone tissue during implantation of the staple legs.

Yet another object is to provide a method for stapling that maximizes the capability of establishing a dynamic compression level that is optimal for enhanced osseous healing.

A still further object is to provide simple, effective bone fixation technique that is relatively easy to learn and practice.

Another object is to provide for compression fixation in applications where other techniques would not work or would not deliver compression. For example, conventional fastening techniques for handling a 'Jones' fracture, i.e. one that is transverse to the longitudinal extent of the bone segment, is difficult to address using conventional fastening techniques, however the present invention is particularly suitable to provide fastening for such fractures.

Still another object is to provide stapling apparatus and method in which there is enhanced selection capability regarding the level of the compressive forces to be imparted.

There are a number of advantages in exterior bone fixation techniques, where surgical incisions are not required and fasteners are applied through the skin; and thus it is yet another object of the invention to provide a bone stapling method that lends itself well to exterior bone fixation.

These and other objects of the present invention are achievable by way of the present invention of a bone stapling method and apparatus that uses a generally U-shaped staple having pair of spaced apart legs with sharp free ends and proximal ends interconnected by bridge that has at least one resilient curved portion, whereby spreading apart of the parallel legs lessens the curvature of the curved portions which brings the staple to a tensioned configuration in which one leg is resiliently urged towards the other. In a preferred embodiment it is seen that the bridge portion comprises a single bowed spring element, the curvature of which lies in a plane normal to the axes of the staple legs.

The novel fastening method involves first positioning the fractured ends of a first and a second bone segment in proximate, face-to-face relationship. The next step involves spreading apart the staple legs by a certain amount and holding the staple in the resultant tensioned configuration. The extent to which the staple legs are separated can be varied in one preferred embodiment of the invention, the induced compressive forces between the legs being proportional to the amount of displacement of the legs as the bowed portion is moved through range of motion in which elastic behavior is exhibited. In this regard it should be evident that herein lies one of the advantages of the present invention, i.e. the capability of selecting the optimal compressive force for an application by spreading apart the staple legs by a predetermined amount.

Next, as the staple is held in its tensioned configuration, it is positioned with it sharp ends forward and aligned respectively with surfaces of one bone segments and the other. Finally the positioned staple, while maintained in its tensioned configuration, is driven into the bone by percussive force, such quick application being provided by a conventional air-powered striker of a stapler according to the present invention, or by a manually stuck staple applicator according to the invention. The embedded staple legs will cause the opposing bone faces to be pressed into each other with a predetermined amount of force.

Such stapling method lends itself advantageously to a staple with a relatively narrow profile, wherein apparatus according to the present invention include a staple applicator having within its housing means for supporting the staple and guiding its movement with legs pointed ends forwardly disposed, and adapted to receive the staple in its initial un-tensioned configuration engaging its legs and spreading them apart by certain amount and holding the staple in its tensioned configuration adjacent the front end of the housing, for ejection therefrom. One embodiment, of several, uses opposing first and second grooves for engaging the staple legs and means for adjustably moving one groove from the other. Another embodiment employs grooves that diverge to spread the staple legs as a staple is advanced there-along. Ejection means mounted for longitudinal movement in the housing has a front end adapted to strike the rear of the tensioned staple with percussive force which is provided by air power or electrical power in preferred embodiments.

The invention also includes a staple applicator that is adapted for being manually driven.

BRIEF DESCRIPTION OF THE DRAWINGS

FIG. 10 is an enlarged, partial perspective view of the front portion of another variant of a staple applicator according to the present invention;

FIG. 11 is a top plan view of a manually powered stapler according to the present invention;

FIG. 12 is a partial, enlarged perspective view of the front portion of the staple applicator of FIG. 11; and FIG. 13 is a sectional view taken along the line 13—13 of FIG. 12.

DETAILED DESCRIPTION OF THE INVENTION

Figure 1:
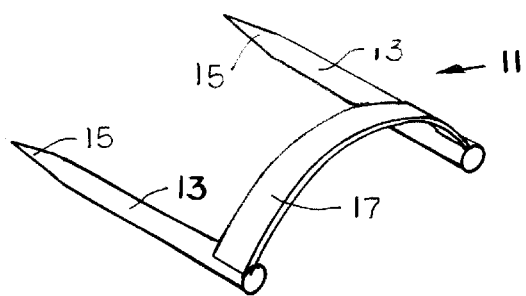
FIG. 1 is perspective view of a preferred embodiment of a compression staple according to the present invention.
Figure 3:
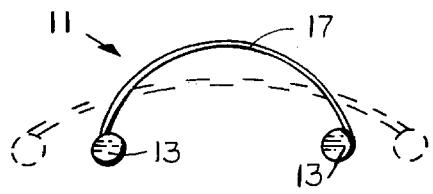
FIG. 3 is a rear end elevational view of the staple of FIG. 1.
Figure 2:
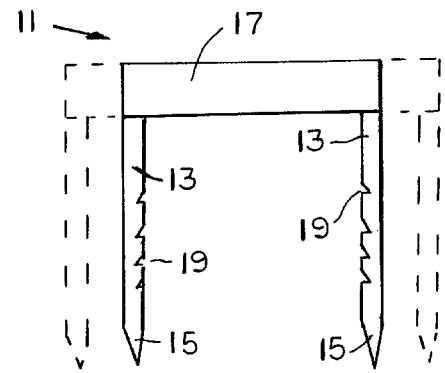
FIG. 2 is top plan view of the embodiment of the staple of FIG. 1.

Referring now the drawings, FIGS. 1–3 show that a preferred embodiment of a compression staple 11 according to the present invention has a pair of legs 13 with sharp front ends 15 and a bridge 17 that interconnects the rear end portions of legs 13. Staple 11 is fabricated of a surgical grade, bio-compatible metal, such as stainless steel, titanium alloy or other suitable alloy. Bridge 17 functions not only to hold legs 13 in approximate parallel relationship, but is selected to act as a spring by the flexing of its bow when the legs are spread apart as illustrated by the broken line image of FIGS. 2 and 3. This imparts an inward reacting force between the legs proportional to the degree of their displacement. It will be appreciated that the dimensions, gauge and curvature of bridge 17 are selected such that it can be flexed to a tensioned state that will deliver the compression requirements of the bone fixation to which staple 11 is to be applied.

It is preferred that the opposing inside surfaces of legs 13 are provided with serrations or barbs 19. In this regard it is noted that, inasmuch as the insides of legs 13 will be pressed against bone mass when they are embedded in a manner to be described, the size of such serrations or barbs can be advantageously minimized, which minimizes trauma to the bone tissue during their implantation.

Figure 4:
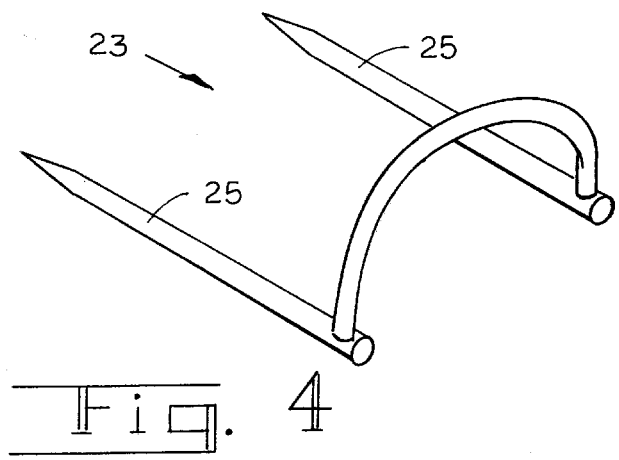
FIG. 4 is a perspective view of variant of a staple according to the present invention.

It will be evident that there can be several variations of compression staples according to the principles of the invention. For example, staple legs can have various cross sectional configurations, including diamond-shaped, square, triangular and rectangular. FIG. 4 shows a variant 23 of a staple according to the present invention, having legs 25. It is formed from metal rod having suitable strength and spring properties. It is also contemplated under the invention that the curvature of the bridge can take other forms than the single bow shown, and would include, among others a generally V-shape and a shape with double 90 degree bends.

Figure 5:
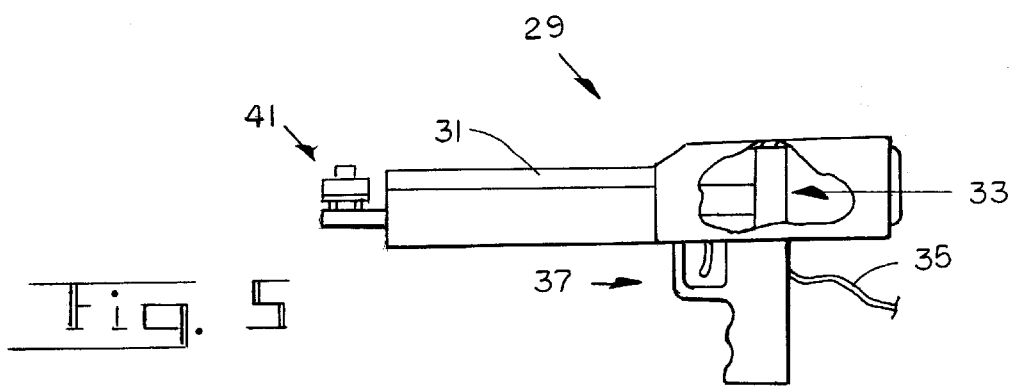
FIG. 5 is an elevational view of staple applicator according to the present invention, with parts broken away for the sake of clarity.

FIG. 5 shows an air-powered staple applicator 29 for applying staple 11, and it includes main body 31, a conventional air piston assembly 33 within body 31, air supply line 35 and a pistol grip and trigger assembly 37 for holding the stapler and for controlling the air-powered operation of the staple head 41, to be described hereinafter.

Figure 6:
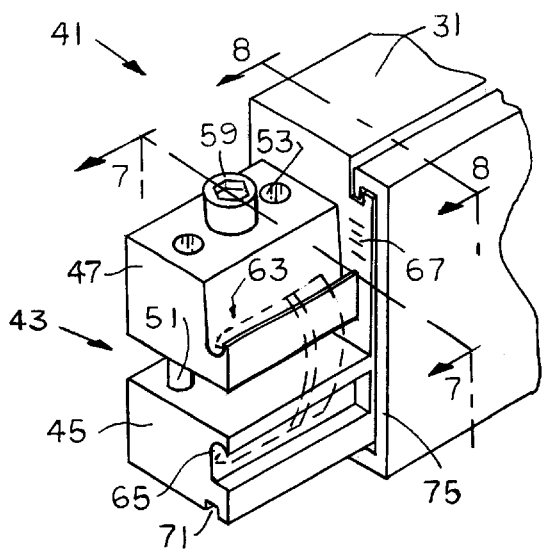
FIG. 6 is a partial, perspective enlarged view of the front end of the staple applicator of FIG. 5.
Figure 7:
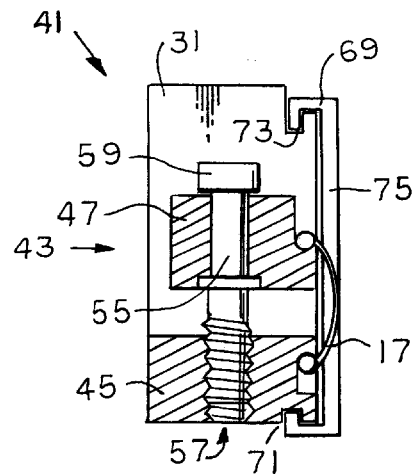
FIG. 7 is a sectional view taken long the line 7—7 of FIG. 6.

As FIG. 6 illustrates, the staple head 41 features an adjustable staple mount 43 that includes lower head 45 which is a forward extension of body 31, and upper head 47. A pair of parallel guide rods 51, affixed to lower head 45 and extending upwardly therefrom, slidably engage twin bores 53 in the upper head 47 so as to guide the upper head in vertical motion relative to the lower head 45. A screw jack assembly drives the upper head and includes thrust screw 55 that engages the threaded bore 57 in lower head 45. FIG. 7 best illustrates the screw jack assembly and shows turn knob 59 that has a socket for receiving a tool such as an Allen wrench for rotating the knob 59. FIGS. 6 and 7 also show a longitudinally extending groove 65 on the lower head 45 and a corresponding parallel groove 63 on the movable upper head 47, these grooves being shaped to cradle the opposing sides of staple legs 13, and the knob can be operated to set the spacing between grooves to allow staple 11, in its initial un-tensioned configuration, to be mounted thereon as illustrated.

In a preferred embodiment, vertically extending gradations are provided at 67 on a forward surface of body 31, adjacent the movable rear end of upper head 45, so as to gauge the displacement of the staple legs when the invention is operated in a manner to be described below.

Figure 8:
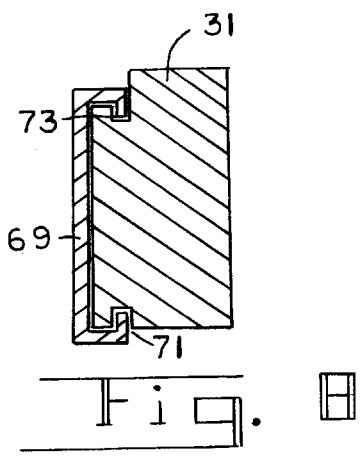
FIG. 8 is sectional view taken long the line 8—8 of FIG. 6.

As FIGS. 6 and 7 and 8 also show, staple applicator 29 includes mechanism for driving a staple forwardly from the staple head 41, and includes longitudinally extending striker member 69 that is slidably mounted to grooves 71 and 73 for longitudinal movement, and the rear portion (not shown), is connected to the air piston assembly, and spring means (not shown) will hold the striker in an initial rearward position as illustrated in FIG. 6. Striker member 69 has front surface 75 that is adapted, as best shown in FIG. 7, to impact the rear legs of the staple bridge 17 when the striker member 69 is propelled to its forward position shown by the phantom lines in FIG. 6.

In the operation of staple applicator 29 for osteosynthesis, a staple 11 is mounted to the staple mount 43 which is operated to bring the staple to the desired tensioned configuration. Then bone segments are brought together by manual or mechanical manipulation as close as possible and aligned with each other. The stapler head 41 can then be positioned with its legs straddling the fracture line, and sharp ends 15 adjacent the surfaces of the bone segments. The stapler trigger can then be operated to cause the striker to drive the legs of the tensioned staple into the bone segments.

Figure 9:
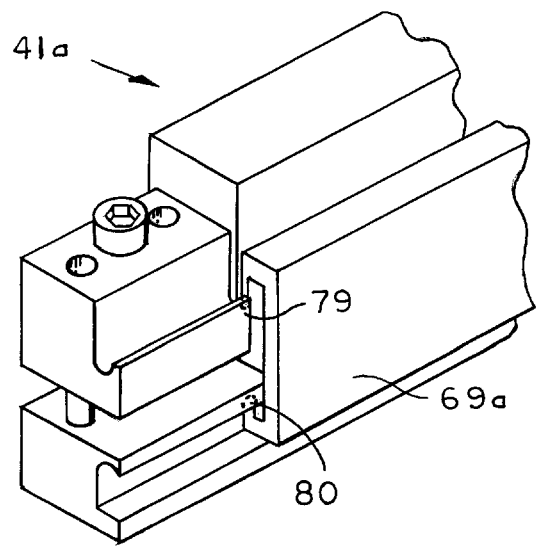
FIG. 9 is an enlarged, partial perspective view of the front portion of a variant of a staple applicator according to the present invention.

There is a variant of a staple applicator according to the invention that is identical to the embodiment of FIGS. 6 and 7, except that it has a striker member 69a is designed to engage the rear ends of staple legs 13 instead of the rear edge of the staple bridge 17. Thus the sectional view of FIG. 9 shows ends 79 and 80 that are adapted to strike respectively the upper and lower rear ends of staple legs 13, of a staple 11 supported in tensioned configuration. It is contemplated under the invention that strikers like striker 69a, with differently spaced ends 79 and 80 can be provided so that different sized staples can be accommodated.

FIG. 10 shows the forward portion 81 of another variant of a power stapler applicator according to the present invention, having a main body 82, an upper staple guide 83 and lower staple guide 85. Opposing forward portions 87 of the guides are separated by a distance allowing it to hold staple 11 in tensioned configuration, and the rearward portions 89 will hold the staple in its initial configuration. The open-sided portions 91 allow a staple to be loaded by hand unto the staple guides. When the staple is pushed forwardly by hand from portion 89 to portion 87, the divergent portions 93 will cause the spreading apart of the staple legs, and thus a tensioned staple is positioned for ejection.

A striker member 95 has upper and lower edges 97 and 99 slidably engaged in slots 101 and 103 so as to mount the striker member for longitudinal movement. The striker front ends 105 and 107 will align with and abut the rear ends of a tensioned staple.

FIGS. 11, 12 and 13 show a variant 113 of the invention, whereby percussive force is delivered by hand using a suitable mallet. Here the body 115 has a rear portion 117 designed for being struck by a mallet, and staple holder 119 at its front end. FIGS. 12 and 13 show how the holder 119 includes lower portion 121 that has staple leg-receiving groove 129, and an adjustable upper part 135 with groove 137. FIG. 12 best shows how a dove-tail portion 141 of part 135 fits in a complementary slot for guiding vertical movement of part 135. Front surfaces 145 and 147 respectively of parts 121 and 135 are adapted to abut the rear ends of a staple mounted in grooves 137 and 129. A screw 153 for driving the part 135 has threads 157 that engage a threaded bore 159 in the movable part 135, and the knob 163 can be engaged by a suitable tool to rotate the screw 153.

In using tool 113 the sharp ends of a tensioned staple 11 can advantageously be precisely positioned on the target spots on the bone segments, then the tool end 117 struck with a mallet to implant the staple.

While particular embodiments of the invention have been described, it should be understood that the invention is not limited thereto, and includes other variants and modifications that will readily occur to those persons of ordinary skill in the art, given the benefit of this disclosure. Thus it is intended that the invention be given its full scope and breath as defined in the claims which follow.

What is claimed is:

1. A stapling method for fastening a first bone segment to a second bone segment, said first bone segment having an end to be connected to an end of said second bone segment said method including the steps of:

a) positioning the end of said first bone segment in face-to-face adjacent relationship with the end of said second bone segment;

b) providing a generally U-shaped staple having a pair of spaced apart legs with sharp free ends and distal other ends interconnected by a bridge that has at least one resilient curved portion;

c) spreading apart said staple legs by a predetermined amount so as to lessen the curvature of said curved portion and to bring said staple to a tensioned configuration in which one leg is resiliently urged towards the other;

d) holding said staple in its tensioned configuration and positioning said tensioned staple with legs generally parallel, and each of the sharp ends of said legs aligned respectively with a spot on the surface of said first and second bone segments; and e) driving and embedding the legs of said tensioned staple into said bone segments and releasing said staple, whereby the opposing faces of the bone segments are caused to be pressed into engagement with a predetermined amount of compressive force.

2. A method as defined in claim 1 wherein the step of driving and embedding of said staple legs is effected by percussion.

3. A method as defined in claim 1 wherein said legs are driven into said bone segments along generally straight, non-divergent paths.

4. A method as defined in claim 1 wherein said legs are held parallel to each other.

5. A method as defined in claim 1 wherein said staple has an initial untensioned condition and said step of spreading apart said legs includes engaging the legs of said staple in its untensioned condition and then moving said staple so that said legs slidably follow a divergent path.

6. A method as defined in claim 1 wherein said staple has an initial untensioned condition and said step of spreading apart said legs includes engaging the legs of said staple in its untensioned condition, and directly moving said legs apart by a predetermined amount.

7. Bone staple applicator for a generally U-shaped staple having a first and a second generally parallel spaced-apart legs with sharp free ends and proximal ends interconnected by a bridge element that has at least one resilient arcuate portion, and said staple having a rear end portion and an initial configuration and capable of a tensioned configuration in which said legs are spread apart from each other by a certain amount whereby the curvature of said resilient arcuate portion is lessened and said spaced-apart legs urged towards each other by certain spring force; said staple applicator including:
   a) a longitudinally extending body with a front end and a rearward end, and including:
      i) means on said body front end for supporting said staple with the sharp ends of its legs forwardly disposed, and for guiding longitudinal movement of said staple and adapted to receive said staple in its initial configuration and for spreading said legs apart by a predetermined amount and holding said staple in its tensioned configuration; and
      ii) ejection means mounted to said body and having a front portion for striking the rear ends of said tensioned staple with percussive force to drive said tensioned staple forwardly from said guide means.

8. Apparatus as defined in claim 7 wherein said means for supporting and guiding said staple includes opposing first and second groove means adapted for engaging respectively the first and second legs of said staple.

9. Apparatus as defined in claim 8 wherein said opposing first and second groove means have rearward portions in which said opposing groove means are spaced apart so as to mount said staple legs of said staple in its initial configuration, mutually diverging portions adapted to move the staple legs from each other as they are slidably pushed there-along, and terminal forward portions for holding said staple in its tensioned configuration.

10. Apparatus as defined in claim 9 including a first support for said first groove means, and a second support for said second groove means, and means engaging said first and second supports for varying the distance between said supports.

11. Apparatus as defined in claim 8 wherein there is plurality of said opposing groove means adapted for handing different widths of said staples.

12. Apparatus as defined in claim 10 wherein said mans for varying the spacing between said first and second groove means comprises drive means, engaging said first and second supports.

13. Apparatus defined in claim 12 wherein said drive means includes drive screw mechanism.

14. Apparatus as defined in claim 12 including means on said body for mounting said first and second groove supports for movement to and from each other and wherein said drive means includes a cam rotatably mounted to said body and said first and second groove supports having opposing cam-following surfaces that engage said cam.

15. Apparatus as defined in claim 7 wherein includes an elongate striker mounted for longitudinal movement on said body, and having a front end adapted for impacting the rearward end portion of said staple.

16. Apparatus as defined in claim 15 wherein said striker is adapted to impact a rear edge of said bridge element.

17. A bone staple applicator for a generally U-shaped staple having a pair of generally parallel spaced apart legs with sharp free ends and proximal ends interconnected by a bridge element that has at least one resilient arcuate portion, and said staple having a rear end portion and an initial configuration and capable of a tensioned configuration in which said legs are spread apart from each other by a certain amount whereby the curvature of said resilient arcuate portion is lessened and said spaced-apart legs urged towards each other by certain spring force; said applicator including:
   a) an elongate body with a front end and a rear end, and including:
      i) means on said body front end for supporting said staple against rearward and lateral movement with the sharp ends of its legs forwardly disposed, with a substantial extent of said legs extending forwardly beyond the front end of said staple supporting means, and including a thrust surface for abutting the rear end portion of said staple, and adapted to receive said staple in its initial configuration and for spreading said legs apart to move said staple to its tensioned configuration and for holding said staple in said tensioned configuration adjacent the ejection end of said support means; and
      ii) said tool having a handle portion, and a rear end adapted for being struck a percussive blow from a hand-wielded mallet.

18. A compression staple for fastening a first bone segment to a second bone segment, said staple having a generally U-shaped configuration and comprising:
   a) first and second spaced-apart longitudinally extending legs with sharp free ends; and
   b) spring bridge means for interconnecting distal end portions of said legs and holding said legs in approximate parallel relationship, and having at least one resilient curved portion whereby spreading apart of said approximate parallel legs lessens the curvature of said at least one resilient portion, causing spring force to urge one leg towards the other.

19. A compression staple as defined in claim 18 wherein said legs each has a longitudinal axis and said axes are contained in a plane which is substantially normal to the plane which contains the line of curvature of said at least one resilient curved portion.

20. A compression staple as defined in claim 18 wherein said spring bridge means has a singular bow configuration.

* * * * *